United States Patent [19]
Smith et al.

[11] Patent Number: 5,538,732
[45] Date of Patent: Jul. 23, 1996

[54] MEDICATED APPLICATOR SHEET FOR TOPICAL DRUG DELIVERY

[75] Inventors: James A. Smith, Chatham, Mass.; Robert W. Kline, Fort Washington, Pa.

[73] Assignee: Creative Products Resource, Inc., North Caldwell, N.J.

[21] Appl. No.: 226,698

[22] Filed: Apr. 12, 1994

[51] Int. Cl.$^6$ ............................................. A61K 7/48
[52] U.S. Cl. ........................... 424/402; 424/404; 514/859
[58] Field of Search ........................... 424/404, 402, 424/443, 60; 514/859, 873

[56] References Cited

U.S. PATENT DOCUMENTS

| | | | |
|---|---|---|---|
| 967,688 | 8/1910 | Titherley | 424/443 |
| 2,187,163 | 1/1940 | Langer | 424/401 |
| 2,673,364 | 3/1954 | Diveley | 424/401 |
| 2,933,431 | 4/1960 | Sperouleas | 424/44 B |
| 3,247,058 | 4/1966 | Hyman | 424/404 |
| 3,806,593 | 4/1974 | Swanbeck et al. | 424/401 |
| 3,896,807 | 7/1975 | Buchalter | 424/402 |
| 4,335,115 | 6/1982 | Thompson et al. | 514/859 |
| 4,343,783 | 8/1982 | Hooper et al. | 424/443 |
| 4,462,981 | 7/1984 | Smith | 424/81 |
| 4,478,853 | 10/1984 | Chaussee | 424/358 |
| 4,497,794 | 2/1985 | Kline et al. | 514/859 |
| 4,615,937 | 10/1986 | Bouchette | 424/401 |
| 4,643,939 | 2/1987 | Sugiyama et al. | 424/81 |
| 4,677,120 | 6/1987 | Parish et al. | 514/549 |
| 4,692,329 | 9/1987 | Klein et al. | 424/401 |
| 4,882,221 | 11/1989 | Bogart et al. | 424/443 |
| 4,891,227 | 1/1990 | Thaman et al. | 424/443 |
| 4,891,228 | 1/1990 | Thaman et al. | 424/443 |
| 4,904,524 | 2/1990 | Yoh | 424/443 |
| 4,943,350 | 7/1990 | Bogart et al. | 424/401 |
| 4,948,585 | 8/1990 | Schlein | 424/401 |
| 5,047,249 | 9/1991 | Rothman et al. | 424/543 |
| 5,063,057 | 11/1991 | Spellman et al. | 424/453 |
| 5,242,433 | 9/1993 | Smith et al. | 604/289 |
| 5,254,109 | 10/1993 | Smith et al. | 514/859 |

*Primary Examiner*—Thurman K. Page
*Assistant Examiner*—S. Howard
*Attorney, Agent, or Firm*—Schwegman, Lundberg & Woessner

[57] ABSTRACT

The present invention provides a method for applying a plurality, preferably two, of dermatological agents to the skin from a single dispensing and applicator sheet comprising a plurality of discrete areas comprising at least two dermatological agents which are simultaneously released from the sheet and applied to the afflicted skin area when the sheet is rubbed over wet skin.

29 Claims, 1 Drawing Sheet

MEDICATED APPLICATOR SHEET FOR TOPICAL DRUG DELIVERY

BACKGROUND OF THE INVENTION

Acne is a common inflammatory disease of human skin, and concentrates in skin areas where sebaceous glands are largest, most numerous, and most active. In its milder types, it is a more or less superficial disorder which is evidenced by slight, spotty irritations and ordinary skin hygiene is a satisfactory treatment. However, in the more inflammatory types of acne, bacterial invasion of or about the pilosebaceous follicles occurs and pustules, infected cysts and, in extreme cases, canalizing inflamed and infected sacs appear. These lesions may become extensive and leave permanent, disfiguring scars.

To reduce the severity of acne, various forms of medication have previously been topically applied to the skin. Antibacterial soaps have been used as well as bactericidal agents such as sulfur and resorcinol. Other topical compositions have separately contained benzoyl peroxide, hexachlorophene, erythromycin or neomycin sulfate. None of these prior preparations has been completely effective.

As disclosed by Klein et al. (U.S. Pat. No. 4,497,794), it was discovered that a mixture on the skin of a peroxide, especially benzoyl peroxide and an antibiotic or antibacterial such as clindamycin, neomycin, sodium sulfacetamide, sulfur, tetracycline or erythromycin is particularly beneficial as they can exert a statistically significant synergistic effect. Peroxides inhibit the formation of free fatty acids in the skin, primarily through inactivation of extracellular lipase (via oxidation) necessary to cleave triglycerides into free fatty acids and glycerol. The antibiotic or antibacterial component reduces the concentration of *Corynebacterium acnes* (i.e., *P. acnes*), a normal anaerobic bacteria which is the prime source of the lipase. Instead of the benzoyl peroxide, which is preferred, peroxides such as stabilized hydrogen peroxide and peroxides of organic acids, such as a lauroyl peroxide, may be used.

As disclosed by Klein et al., erythromycin and benzoyl peroxide may be applied to the skin in combination in a preformulated aqueous gel. However, the premix must be used relatively promptly due to the chemical incompatibility of the two active agents. Because of this, it is advisable that the two agents be put in separate vials, bottles or other containers. For example, the Klein et al. patent discloses a kit containing, separately bottled compositions comprising benzoyl peroxide and erthyromycin dissolved in ethanol or acetone. However, separately packaging multiple dosages of the two active ingredients presents a number of disadvantages to the end-user. For example, the pharmacist must compound each prescription refill. This is both time consuming and provides opportunity for spillage, or over- or underdosing. In addition, this pharmacy-compounded system adds cost to the end-user.

Therefore there is a need to develop a method of packaging and delivering of chemically incompatible dermatological agents. To this end, several applicator systems have been developed with a prescored fracture line in one surface of a package which separates the agents in discrete portions of a single package. For example, U.S. Pat. No. 4,140,409 to DeVries discloses a package system for containing and dispensing liquids and other flowable materials comprising a reservoir chamber in each half of an elongated package. A prescored fracture line in one surface of the package ruptures when the ends of the package are urged together, and the contents of the chambers are expelled into an applicator sponge that is attached to the outside of the package. However, a disadvantage of packages with such externally placed applicators is that the applicator may become soiled or detached. Also, where a sterile applicator is desired, such a package system may not maintain the applicator under sanitary conditions prior to use.

Recently, Smith et al. (U.S. Pat. No. 5,242,433) have disclosed an applicator system comprising at least two absorbent pads which are each impregnated with a different dermatological composition, and which are packaged separately in a side-by-side manner, attached to a moisture-impermeable base sheet. When the cover sheet is removed, the pads can be wiped onto the skin of the user, simultaneously releasing and combining the compositions from the pads. However, the construction and loading of this system is relatively complex, requiring that the pads be separately attached to the base sheet impregnated with the compositions, and then covered with a moisture impermeable seal.

Therefore, there is a need for a method of dispensing system which addresses the above mentioned problems of prior dispensing systems. In particular, there is a need for a packaging system for dispensing active ingredients, which has an improved configuration for releasing the contents of the packaging and that is not prone to premature mixture, but provides ready dispensing of the package contents. There is also a need for a packaging that is a convenient means of dispensing a plurality of active ingredients from multiple chambers within the packaging system to overcome the physical or chemical incompatibility of the substances.

SUMMARY OF THE INVENTION

The present invention provides a novel system for containing, dispensing and essentially simultaneously applying two or more compositions which may contain plurality of bioactive agents to a target surface, such as the surface of the skin.

In one embodiment of the invention, there is provided an article of manufacture for applying a plurality of dermatological agents to the skin from one dispensing and applicator system comprising a flexible absorbent base sheet impregnated with first and second solid or semi-solid compositions comprising first and second dermatological agents, each confined to first and second discrete areas, respectively. Preferably, each of said compositions is anhydrous, while being water soluble or water dispersable. The compositions are released from the sheet when the sheet is contacted with wet skin so as to apply a film of a mixture of the dermatological agents to the skin. Alternatively, the sheet may be moistened by the user, just prior to use, and applied to dry skin, so that the agents are released and mixed on the skin.

For example, the present applicator system is particularly well-adapted to contain, preserve, and to simultaneously deliver two or more chemically or physically incompatible active ingredients. Preferably, the medicated sheet will be used to contain, preserve and deliver unit doses of two cosmetic or pharmaceutical ingredients intended for topical application to the skin, e.g., dermatological agents, such as are used to treat a disorder such as acne, dermatitis, insect bites, diaper rash, sunburn, burns and the like.

Methods of using the novel dispensing and applicator systems are also within the scope of the invention.

These and other advantages of the invention over conventional dispensing and application methods will become more apparent after reading the description and claims which follow.

As used herein, the term "dermatological agent" encompasses bioactive compounds, such as antibiotics and peroxides, as well as compounds intended primarily for cosmetic purposes, such as emollients and sunscreens.

All percentages are by weight unless otherwise indicated.

BRIEF DESCRIPTION OF THE DRAWINGS

Throughout the following views, reference numerals will be used on the drawings, and the same reference numerals will be used throughout the several views and in the description to indicate same or like parts of the invention.

DETAILED DESCRIPTION OF THE INVENTION

Figure 1:
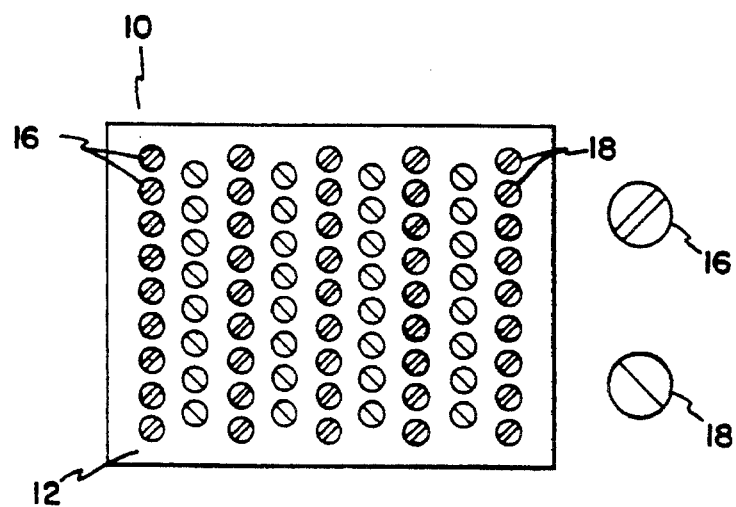
FIG. 1 is a perspective view of the dispensing device of the invention.

Referring now to FIG. 1, the dispensing and applicator device, designated generally by the numeral 10, is shown according to the present invention. As depicted, dispensing and applicator device 10 is of a generally rectangular/trapezoidal configuration. It will be understood, however, that a variety of shapes and sizes can be accommodated according to the invention. Referring to FIG. 1, dispensing and applicator device 10 is shown having a medicated sheet 12 which contains shaped reservoir populations 16, 18. The reservoir populations are preselected areas of the sheet of which each are impregnated with a composition comprising a different dermatological agent. Reservoir populations 16, 18 are arranged in a separated array, such as being positioned adjacent to each other in a side-to-side arrangement on one surface of the medicated sheet 12. The reservoir areas can be positioned on the base sheet in virtually any non-overlapping array, including stripes, dots, diamonds, or some other array. As few as two reservoir areas can be employed, if they are large enough, but preferably, many more will be employed, i.e. 50–100 of each composition type. The sheet can be formed of any flexible absorbent material, including woven and non-woven fabrics and felts, natural fibers, synthetic fibers or a mixture thereof.

Figure 2:
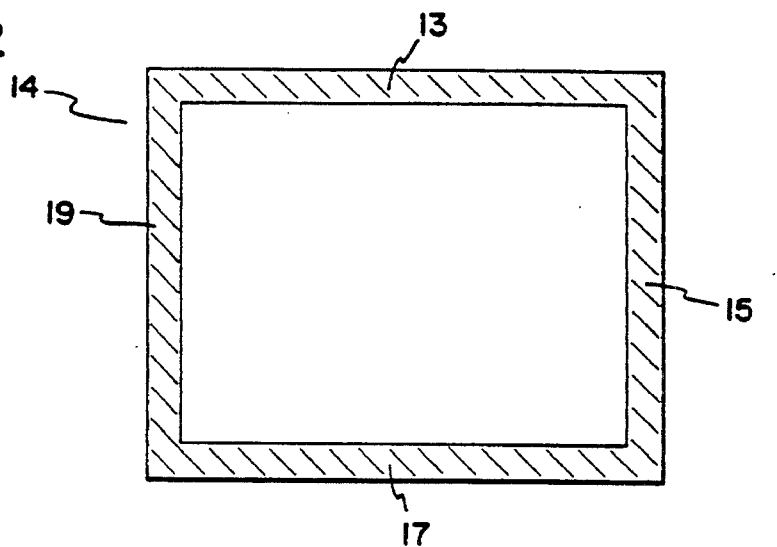
FIG. 2 is a perspective view of the dispensing device of the invention shown in the closed cover envelope.

In one embodiment of the invention, the dispensing and applicator device may be enclosed within a cover envelope to provide the composite device with a sheet carrying a unit dosage form of each of the agents. FIG. 2 illustrates the enclosure of the dispensing and applicator device in such an envelope. The material used for the cover envelope 14 should be relatively puncture resistance, non-absorbent, and impermeable, chemically compatible and non-reactive with the material contained in the dispensing and applicator device 10 to prevent leakage or migration of the contents out of the dispensing and applicator device 10, and substantially impermeable to external contaminants such as air, dust, liquids and the like.

Suitable materials for cover envelope 14 should be materials capable of allowing cover envelope 14 to be sealed to itself along seal lines 13, 15, 17, and 19 in order to form a containing and dispensing package that does not separate during normal use. For example, cover envelope 14 may be made of a thermoplastic and heat sealable polymeric film material, such as polyethylene, polyvinyl chloride, or polyamide-type resins, according to known techniques in the art. Such a film may be used alone or adhered to a non-heat sealable material by known techniques. Cover envelope 14 may be formed, for example, of glassine paper, cellophane, polyethylene, polypropylene, polyvinyl chloride, polyester, nylon and the like. Cover envelope 14 may also be formed of an aluminum foil that is coated or sealed with a thermoplastic material such as a polyethylene, polyester, polyvinyl resin or cellulose acetate. Alternatively, the foil may comprise a cellulosic material lined with a thermoplastic film or other synthetic or plastic material. A foil-lined paper board may also be used. For examples of flexible materials suitable for the cover envelope 14, see for example, "Coatings and Laminations," in *Handbook of Package Engineering* (2d ed.), pages 4-1 to 4–20, J. F. Hanlon, the disclosure of which is incorporated by reference herein.

A coating to provide a nonporous gas and/or vapor barrier, as for example polyethylene and/or polyester, may be applied to the outer surface of cover envelope 14. The coating may provide a sealant to prevent exposure of the sheet to environment of contamination.

Cover envelope 14 may be sealed to itself by a heat seal, pressure seal, high frequency seal, ultrasonic seal, a crimp, a bonding material or various adhesive materials. Other suitable attachment method or means, may be used to effect a secure seal according to known techniques in the art. For example, heat may be applied according to known techniques in the art to cause a bonding of the thermoplastic liner of cover envelope 14 to itself. A temporary heat seal may be formed by applying relatively narrow lines of heat seal, and wider lines of heat seal may be applied to effect a more permanent may also be provided by applying a high degree of heat using an appropriately high temperature, and a lower degree of heat using a lower temperature to provide a temporary seal.

Adhesives used to form seal lines 13, 15, 17, and 19 should be non-reactive and compatible with the material used for cover envelope 14 as well as with the contents within the compartment or subcompartments of dispensing and applicator device 10, and should not permit premature leakage or diffusion of such materials from the package. An example of adhesives for affecting a releasable seal include, for example, polyvinyl chloride (PVC) applied to one surface, and polyvinyl acetate applied to a second surface. Cover envelope 14 may also be sealed together by a piece of material (not shown) attached between the two surfaces of cover envelope 14.

Figure 3:
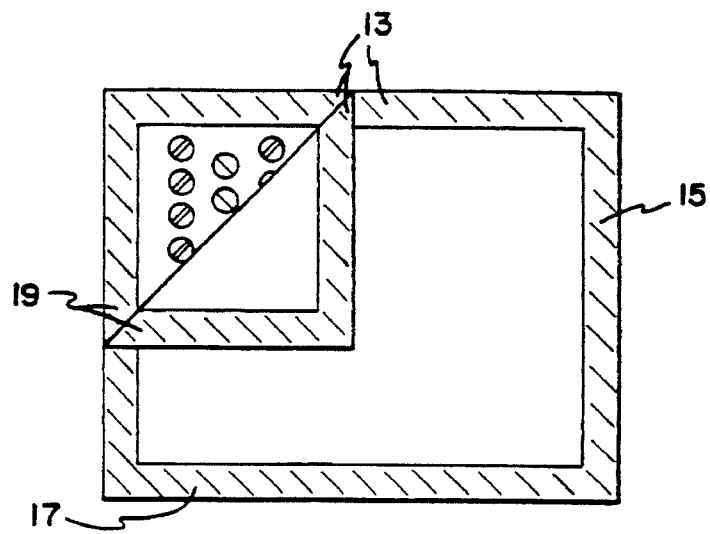
FIG. 3 is a perspective view of the dispensing device of the invention shown in a partially opened cover envelope.

It is understood according to the invention that reservoir populations 16, 18 may each contain the same or different substances. Advantageously, the dispensing and applicator device 10 of the invention may be used to dispense two or more substances that should be, or are preferably, kept separated until the desired application. The two components would then be dispensed simultaneously from the reservoir populations 16, 18 in the embodiment shown in FIGS. 1 and 3. A wide variety of different cosmetic or bioactive agents may be impregnated in reservoir populations 16, 18, as well be discussed hereinbelow.

As exemplified, the present applicator sheet can readily retain, preserve and deliver single unit doses of two or more chemically- or physically-incompatible active ingredients. For example, antibiotic in combination with a liquid, semi-liquid (cream) or gelled aqueous or preferably a non-aqueous vehicle can be absorbed by and retained in the first reservoir population a second ingredient which is physically- or chemically-incompatible with the antibiotic, such as a peroxide, can be absorbed and retained in the second reservoir population, preferably in combination with the appropriate vehicle. Following absorption of the compositions into the reservoir areas, the sheet may be dried to remove any water from the compositions. The finished sheets are essentially dry and non-oily to the touch.

Other examples of pairs of such ingredients include (a) an antibiotic or a peroxide for treatment of a skin disorder and a keratolytic/antiseptic agent such as salicylic acid; (b) retinoic acid (Retin® A) and moisturizing agent to counteract the drying/scaling effects of the Retin® A, and/or a sunscreen to protect the skin against the increased sensitivity to the sun caused by the Retin® A, (c) asteroid, preferably a corticosteroid and a complementary dermatological agent, such as an antihistamine, antifungal, antibiotic and/or sunscreen.

As can be readily be seen from the figures, the present applicator is adapted to simultaneously release and produce a mixture of two (or more) active ingredients on the target skin area to be treated.

Although each reservoir will contain at least one active ingredient, preferably in combination with a suitable carrier vehicle, compositions containing multiple active, chemically compatible ingredients can be absorbed onto each of one or more reservoir populations on the sheet.

Compositions for Acne Treatment

I. Peroxide

One reservoir population of the present acne-treatment applicator sheet will preferably comprise an effective fatty-acid-inhibiting amount of a peroxide, i.e., hydrogen peroxide or an organic peroxide, preferably in combination with a gelled or semi-liquid (lotion or cream) vehicle. The peroxide compound can be essentially pure, or can be stabilized, e.g., by absorption on an inert particulate carrier.

No matter what vehicle is employed, on a weight basis, the selected antibiotic (clindamycin, tetracycline and/or erythromycin) and the selected peroxide should be measured out so that as applied to the skin, the latter is from about one to about thirty times the weight of the former, preferably from about one to about five times. Thus, in the first reservoir population, the selected antibiotic should be present at a level ranging from 0.5% to 10% w/w of the total composition absorbed into the sheet, and, on the second population, the selected peroxide should be present at a level ranging from 1% to 30% w/w of the total composition absorbed into the sheet. A preferred concentration is about 5% to about 10% of the selected antibiotic and about 15% to about 20% of the selected peroxide, based on the total weight of each of the compositions which are used to impregnate the sheets.

A. Anhydrous Emollient Peroxide Gel

A preferred peroxide-containing composition for use in one of the reservoir populations of the present applicator system comprises an effective anti-acne amount (about 1–20%, preferably 12.5–17.5%) of an organic peroxide, preferably benzoyl peroxide dispersed in an essentially water-free blend of surfactants, along with about 20–30% of the organic gelling agent. Such gels can comprise about 40–50% of a mixture of organic emollient oils, about 10–20% peroxide, 10–15% of linear fatty alcohol, and, optionally, about 1–5% of a nonionic surfactant.

These gels are "anhydrous" in the sense that the only water present is provided via the commercially available forms of the emollient esters and surfactants, and is preferably ≦5%, most preferably ≦2.5%, of the total gel. The water content can further be lowered by drying the finished applicator sheet at temperatures that do not decompose the active agents.

1. Emollient Oils

Useful emollient oils for incorporation into the aqueous reactant phase include those water-insoluble liquids which can function to soften the skin of the user and provide a degree of barrier protection against environmental irritants.

Preferred emollients oils for use in the present invention include mixtures of emollient organic esters and ethers. Preferred emollient esters include those organic esters that can also function as nonionic surfactants. They include about 0.5–5% of polyoxyethylene ($C_8$–$C_{12}$) fatty acid esters of glycerol, such as steryl stearate (Liponate SS, Lipo), Pentaerythritol tetrastearate (Liponate Ps-4, Lipo), PEG-7 glyceryl cocoate (Cetiol® HE, Henkel), PEG-30 glyceryl cocoate, PEG-12 glyceryl laurate, PEG-20 glyceryl oleate, and the like, wherein the number designates the approximate number of oxyethylene moieties present.

Other useful emollient esters include ($C_5$–$C_{30}$)-alkyl, ($C_8$–$C_{22}$)fatty acid esters, wherein the fatty acid moiety is optionally substituted with a ($C_8$–$C_{22}$)alkanoyl group. Such esters are commercially available, e.g., as Ceraphyll® 847 [2-octyl(dodecyl)] (12-steroyl-stearate), Ceraphyll® 368 (2-ethylhexylpalmitate) and Ceraphyll® 230 (isocetyl stearate) from Van Dyk & Co., Belleville, N.J. Preferably, the aqueous reactant phase will include about 5–50% by weight of these fatty acid esters, most preferably about 10–45%.

Other useful classes of water-insoluble emollient esters include the ($C_8$–$C_{22}$)fatty acid esters of propylene glycol, e.g., propylene glycol dicaprylate/dicaprate (Edenol® 302); the ($C_6$–$C_{12}$)fatty alcohol esters of hydroxy ($C_8$–$C_{22}$)fatty acids, e.g., octylhydroxy stearate (Naturechem® DHS); the esters of fatty alcohol(polyethylene oxideethers) with fatty acids, e.g., myreth-3-caprate, myreth-3-myristate and myeth-3-myristate (Cetiol® 1414-E, Henkel), wherein the number indicates the number of oxyethylene moieties present; the benzyl alcohol esters of one or more $C_{10}$–$C_{20}$ fatty acids, e.g., benzyl linoleate (Dermol® 618, Alzo, Inc., Matawan, N.J.); the fatty alcohol esters of benzoic acids such as the $C_{12}$–$C_{15}$ alkylbenzoates (Finsolv® TN, Finetex, Inc.) described in U.S. Pat. Nos. 4,278,655 and 4,275,222; the liquid fatty alcohol esters of $C_3$–$C_6$ aliphatic carboxylic acids, i.e., isodecyl neopentanoate (Dermol® 105); and the ($C_1$–$C_3$)alkanol di- or triesters of dimer or trimer acid (the dimer or trimer of oleic acid). Such esters are commercially available as Schercemol® TT (triisopropyl trimerate) and Schercemol® DID (diisopropyl dimerate, Scher Chemicals, Clifton, N.J.). The liquid fatty acid-esters of dimer acid may also be successfully employed in the present compositions, e.g., the diisostearyl ester of dimer acid, Schercemol® DISD.

A preferred class of emollient ethers are the polyoxypropylene, polyoxyethylene ethers of lanolin or of ($C_8$–$C_{22}$) fatty alcohols, such as PP5-5-Ceteth-20 which is the ether of cetyl alcohol having 20 ethylenoxy units and 5 propylenoxy units (Procetyl® AWS, Croda), Lipocol C-2® (Ceteth-2, Lipo Chemical) and Lanexol® AWS (PPG-12-PEG-50 lanolin, Croda). These mixed polyalkylenoxy ethers may be present at about 0.1–0.5% of the total peroxide-containing gelled vehicle.

2. Surfactant

Surfactants may also be used to stabilize the gelled composition. A preferred class of surfactants is the anionic surfactants, including the $C_{14}$–$C_{18}$ primary alkyl sulfates, such as sodium lauryl sulfate, sodium cetyl sulfate and sodium stearyl sulfate. Commercially available anionic surfactants of this class include DEA-Laureth Sulfate and Cocamide-DEA (Monamine 779, Mona).

Another preferred class of these materials is fatty acid amides such as the mono- and dialkanolamides of $C_8$–$C_{22}$ fatty aids, e.g., a mono- or di($C_2$–$C_4$)alkanol-amide. Commercially available, nonionic surfactants of this class include lauramide DEA (Standamid™ LP, Henkel), lauramide MEA (Monamid™ LMA, Mona), lauramide MIPA (Monamid™ LIPA, Mona), myrisamide MEA, myristamide MIPA, Myristamide DEA, Oleamide DEA, oleamide MEA, oleamide MIPA, cocamide MEA, cocamide DEA, cocamide MIPA, stearamide MEA, stearamide MIPA, stearamide DEA and the like.

Other useful nonionic surfactants include the amine oxides, such as the $C_{10}$–$C_{20}$-alkyl-di(lower)alkyl-amine oxides or the [$C_{10}$–$C_{20}$-alkylamido, ($C_2$–$C_5$)alkyl]di(lower) alkyl-amine oxides. Especially preferred members of this class include lauryl (dimethyl) amine oxide, myristyl(dimethyl)amine oxide, stearyl(dimethyl)amine oxide (Schercamox™ DMS, Scher Chemicals, Inc., Clifton, N.J.); coco-(bis-hydroxyethyl)amine oxide (Schercamox™ CMS), tallow(bis-hydroxyethyl)amine oxide and cocoamidopropyl(dimethyl)amine oxide (Schercamox® C-AA).

3. Gelling Agents

The present peroxide-containing vehicles will comprise an amount of an inorganic or organic gelling agent effective to gel or thicken the aqueous-alcoholic mixture to at least a cream- or lotion-like consistency.

Preferably, the organic gelling agents employed will comprise those of natural or synthetic origin. Preferred one of the gelling agents are the starches such as the glyceryl starches which is available commercially as Vulca 90 (National Starch). Other useful organic gelling agents also include microcrystalline cellulose and hydroxyalkyl cellulose ethers such as hydroxypropylmethyl cellulose (HPMC), hydroxymethyl cellulose (HMC), carboxymethyl cellulose (CMC), 2-hydroxyethyl cellulose, 2-hydroxyethylmethyl cellulose, and 2-hydroxypropyl cellulose (Klucel® H).

Organic gelling agents useful in the practice of the present invention also include polyvinylpyrrolidone and polymeric organic waxes. The useful polymeric waxes include ethylene acrylate copolymers, ethylene acrylic acid copolymers and polyethylene (e.g., oxidized polyethylenes). These materials are commercially available in the form of aqueous emulsions or dispersions, e.g., from Allied Chemical, Morristown, N.J., as the A-C Copolymer and A-C Polyethylene series, such as A-C Copolymer 540, A-C Copolymer 580 and A-C Polyethylene 617 and 629. Waxy polyethylene glycols (PEG) such as those of a molecular weight of about 800 to 1700–200 are preferred for use in the present gels.

Preferred gelling agents also include the so-called hydroxylated vinylic polymers, particularly those disclosed in U.S. Pat. No. 2,798,053. Among those hydroxylated vinylic polymers of special interest herein are described generally as interpolymers of a monomeric monoolefinic acrylic acid, and from about 0.1% to about 10% by weight based on the total monomer of a monomeric polyether of an oligosaccharide in which the hydroxyl groups which are modified are esterified with allyl ether groups per oligosaccharide molecule. The Carbomer series is representative of commercially available interpolymers of this type, which are marketed under the trade name Carbopols®. These are described as being polymers of acrylic acid cross-lined with about 1% of a polyallyl ether of sucrose having an average of 5.8 allyl groups for each sucrose molecule. These polymers have molecular weight in the order of magnitude of 1,000,000. Such polymers are available from the B.F. Goodrich Chemical Company and are sold under such trademarks as Carbopol® 934, Carbopol® 940, Carbopol® 941 and Carbopol® 934P.

Preferably, the inorganic gelling agents employed will comprise those natural or synthetic agents of mineral origin. Preferred gelling agents are the montomorillonite clays such as the saponites, hectorires, laponites and the montomorillonite colloidal clays such as Veegum™ (Vanderbilt Minerals, Murray, Ky.) or Magnabrite™ (American Celloid Co., Skokie, Ill.). Clay-based gellants containing montmorillonite and aluminum hydrosilicate together with suborganic radicals are available as the Tixogel™ series (United Catalysts, Louisville, Ky.). A useful montmorillonite clay gelling agent is a bentonire such as Korthix™ H (Kaopolite, Inc., Union, N.J.). Inosilicates can also be used, alone or in combination, with the clays. Preferred inosilicates are the naturally-occurring calcium metasilicates such as wollastonite, available as the NYAD™ wollastonite series (Processed Minerals Inc., Willsboro, N.Y.). Synthetic sodium magnesium silicate clays, alumina, magnesium aluminum silicate, and fumed silicas can also be used as gelling agents.

The quantity of gelling agent that may be contained in the present compositions may also vary somewhat. Ordinarily, this will constitute about 5% to about 20% by weight, and preferably about 20% to about 25% by weight, based on the total weight of the finished peroxide-containing vehicle.

A typical formulation for a waxy anhydrous benzoyl peroxide formulation is given on Table I, below. The formulation contains 35% benzoyl peroxide, and has the consistency of a light gel.

TABLE I

| INGREDIENTS | CTFA CHEMICAL NAME* | % |
|---|---|---|
| Myritol 318 | Caprylic/Capric Triglycerides | 7.89 |
| Procetyl AWS | PPG-5-Ceteth-20 | 7.08 |
| Lipocol C-2 | Ceteth-2 | 4.24 |
| Crodacol CS-50 | Cetearyl Alcohol | 11.94 |
| Liponate SS | Stearyl Stearate | 11.13 |
| Liponate PS-4 | Pentaerythritol Tetrastearate | 19.80 |
| Vulca 90 Starch | Glyceryl Starch | 23.62 |
| Benzoyl Peroxide (35%)** | — | 14.30 |
| | | 100.00 |

*See CTFA Cosmetic Ingredient Dictionary, N. F. Estrin, ed., The Cosmetic, Toiletry and Fragrance Association, Inc., pub., Washington, D.C. (3d ed. 1982).
**Stabilized with dicalcium phosphate (Akzo).

To prepare this formulation, the Myritol, Procetyl, Lipocol C-2, Crodacol and Liponates are added to a suitable water bath flask with vigorous stirring. The mixture is heated gradually to 55°–58° C., until all the ingredients are melted with continued stirring. The starch is then added slowly to the mixture stirring with good agitation, and once the starch is efficiently mixed in, the benzoyl peroxide is added slowly with continued stirring until it is dispersed uniformly. The composition is maintained at 57°–58° C. and is applied to a porous nonwoven fabric or proper base sheet in an array of circular reservoirs (about 75 on a 4-inch square sheet). Each sheet contains about 0.6 g of peroxide.

II. Antibiotic

Preferred medicated sheets intended for acne treatment will comprise a population of reservoirs comprising an absorbed aqueous, alcoholic, or aqueous-alcoholic solution of the antibiotic, which are then dried to an anhydrous state. Erythromycin, tetracycline, meclocycline, clindamycin and the pharmaceutically acceptable salts thereof are preferred. Useful salts include the salts of inorganic or organic acids, such as the hydrochloride, phosphate, glyconate, citrate, maleate, stearate, and hydrobromide salts. Antibiotics stabilized by encapsulation of the particles of active ingredient by non-toxic water-soluble polymers are particularly useful.

Useful alcohols include ethanol, isopropanol and mixtures thereof. Benzyl alcohol and/or butanol can also be used in combination with varying amounts of water. All, or a part of the alcohol, can be replaced by other volatile water-miscible organic solvents such as m-pyrol, liquid polyethylene glycols, acetone, THFA and the like.

The antibiotic or salt thereof will preferably be dissolved or dispersed in the solvent or solvent system at a concentration effective to significantly decrease the skin concentration of *Corynebacterium acnes* upon topical application of the sheet to yield about 0.5–10 mls of the reconstituted antibiotic solution on the wet skin of the afflicted human or animal. Preferably, an effective amount of about a 0.5%–10% solution or dispersion of the antibiotic, is formed on the skin upon application by the user.

Emollient organic esters are preferably also self-emulsified into an alcohol system, e.g., one comprising about 10–25% fatty alcohol, about 45–55% emollient organic oil, about 20–30% of an organic gelling agent (i.e., a modified starch) about 5–10% antibiotic, in order to provide anhydrous reservoir areas which give the sheet a better skin-feel and aid in the even distribution of the antibiotic on the skin. Optionally 1–5% of an anionic surfactant, such as the amine salt of an alkylsulfonic acid, is added to adjust the pH. A typical emollient formulation comprising about 3% erythromycin is given on Table II, below.

TABLE II

| INGREDIENTS | CTFA CHEMICAL NAME* | % |
| --- | --- | --- |
| Myritol 318 | Caprylic/Capric Triglycerides | 9.33 |
| Procetyl AWS | PPG-5-Ceteth-20 | 7.10 |
| Lipocol C-2 | Ceteth-2 | 3.33 |
| Crodacol CS-50 | Cetearyl Alcohol | 11.94 |
| Liponate SS | Stearyl Stearate | 11.13 |
| Liponate PS-4 | Pentaerythritol Tetrastearate | 19.80 |
| Monamine 779 | DEA-Laureth Sulfate and Cocamide DEA | 2.07 |
| Vulca 90 Starch | Glyceryl Starch | 27.97 |
| Erythromycin (45%)* | — | 7.33 |
| | | 100.00 |

*Encapsulated in a water soluble coating (Encapsulation Technologies, Inc.)

To prepare this formulation, Myritol, Procetyl AWS, Lipocol, Crodacol and both Liponates are added to an appropriate flask equipped with a stirrer and hot water bath. The mixture is heated to 60° C. until uniform with stirring. The Monamine 779 is then added which adjusts the pH of the final product to a physiologically-acceptable pH. The starch is then added slowly with continuous agitation and the temperature dropped to about 56° C. Erythromycin-encapsulated powder is then added while maintaining the temperature between 55° C. and 57° C. The melting point of the composition after it is applied to the porous peroxide-containing sheet disclosed above, and solidifies, is above 40° C., so that the resultant reservoir areas do not run or bleed during storage. About 75 circular reservoirs can be applied to a 4-inch square porous paper or fabric sheet. Each sheet then contains about 0.6 g of erythromycin.

Clindamycin phosphate tetracycline or meclocyline can replace erythromycin in this formulation.

III. Keratolytic Agents

In medicated sheets intended for ache treatment, the antibiotic or benzoyl peroxide composition can be replaced with a composition containing another non-peroxide keratolytic agent such as salicyclic acid, azelaic acid, resorcinol, sulfur, trichloroacetic acid, alpha-hydroxy-acids such as citric acid or lactic acid or mixtures thereof, which acts as an antiseptic, an antifungal and a topical keratolytic agent. A suitable vehicle for these acids can be prepared by mixing water with a gelling agent and adding a water-miscible organic solvent in a weight ration of about 0.–4 parts water to 1.9 part solvent, e.g., a ($C_2$–$C_4$) alkanol. The acids are dispersed in this mixture at about 0.5–10% of the finished composition. Two typical salicyclic acid formulations are given on Table III, below.

TABLE III

| Ingredients | CTFA Chemical Name | A % | B % |
| --- | --- | --- | --- |
| Water, distilled | — | 74.57 | 12.62 |
| Klucel H | Hydroxypropyl-cellulose | 1.52 | — |
| Carbopol 934P NF | Carbomer 934P | — | 1.95 |
| Isopropanol | Isopropyl Alcohol | 21.74 | 82.52 |
| Salicylic Acid | — | 2.17 | 2.91 |
| Powder U.S.P. | | | |
| Total | | 100.00 | 100.00 |

Formulation B yielded a light, fluid gel that spread into an even film. Formulation A yielded a thicker, fluid gel.

IV. Retinoic Acid

As disclosed hereinabove, for the topical treatment of acne using the present dispensing an applicator system, one of the reservoir populations may contain solid, semi-solid or gelled formulation comprising an effective anti-acne amount of retinoic acid, while the other reservoir population or populations preferably contain an emollient composition to counteract the drying/scaling properties of the retinoic acid, and/or an effective amount of a sunscreen composition to protect the user from retinoic acid-induced sensitivity to UV light.

Useful retinoic acid compositions can be formulated as creams or gels; preferably comprising about 0.01–0.25 wt-% of retinoic acid. Useful gels can be formed in aqueous, water-miscible organic solvent vehicles comprising water:solvent ratios of about 9:1 to 1:9, in combination with an effective amount of an organic and/or inorganic gelling agent, of the classes described hereinabove. Retinoic acid-containing liquids can simply be prepared by dissolving an effective amount of retinoic acid in water organic solvent, using nontoxic organic solvents, such as the ($C_2$–$C_4$)alkanols and liquid polyoxyethylene glycols disclosed hereinabove. Due to the unstable nature of retinoic acid, minor but effective amounts of antioxidants, such as BHT, are preferably included in these formulations.

V. Skin Moisturizing Composition/Sunscreens

Emollient compositions which soften and protect the skin are preferably used in conjunction with a dermatological composition comprising retinoic acid, or as a carrier vehicle for retinoic acid. When used in conjunction with retinoic acid, the emollient compositions preferably include an effective amount, i.e., 1–10 wt-% of one or more, i.e., 1–3 sunscreen compounds. These include oxybenzone, ethyldihydroxypropyl-p-amino benzoate, octyl dimethyl-p-aminobenzoate, para-aminobenzoic acid, and the like. Useful emollient compositions include those disclosed in Smith et al. (U.S. Pat. No. 4,559,157) which are oil-in-water emulsions comprising an oil phase containing at least one emollient oil and at least one emollient wax stabilizer, dispersed in an aqueous phase comprising at least one polyhydric alcohol emollient and at least one amphoteric (amine oxide) or anionic surfactant. Effective amounts of bactericidal preservatives and fragrance may also be employed in the impregnating emulsion. These emulsions are formulated so that an effective amount of emollients and fragrance is released and evenly coated onto the skin with no "skipping" or separation when the impregnated sheet is pressed or rubbed against a moist skin surface. This requires that the emulsion be formulated so that it will be stable and not break when mixed with the additional water present on the skin due to bathing, showering or the like.

It has been found that emollient emulsions stable under these conditions can be formulated by dispersing an oil phase comprising one or more emollient oils and one or more emollient wax stabilizers in an aqueous phase comprising one or more polyhydric alcohol emollients and one or more water-soluble organic surfactants.

Therefore, the emulsions of the present invention preferably will comprise about 15–50% of water-insoluble or soluble active ingredients, i.e., the emollients, surfactants, fragrance and preservatives; and 50–85% water, preferably distilled or deionized water. About 7–20% of the active ingredients will be present as the oil phase of the emulsion, while the remainder of the active ingredients will be fully soluble in the water phase. Emollients will preferably comprise about 10–50% by weight of the emulsions. Emollients useful in the practice of the present invention are generally described by G. Barnet, Emollient Creams and Lotions, and by S. J. Strianze, Hand Creams and Lotions, in *Cosmetics— Science and Technology*, Wiley Interscience Pub. (1957) at pages 99–181.

VI. Emollient Wax Stabilizer

The emollient oils useful in these compositions have been described hereinabove. Emollient wax stabilizers are waxy solids at room temperature. They function to soften and smooth the skin surface and to prevent evaporation of interior skin moisture. They also can function as nonionic emulsifying agents and act to adjust the final viscosity of the composition. The emollient wax stabilizers useful in the practice of the present invention include beeswax, spermaceti, solid hydrocarbons, $C_{12}$–$C_{18}$ fatty alcohols, glyceryl monostearate, ethylene glycol monostearate, polyethylene glycol distearate and other ($C_{12}$–$C_{18}$) fatty acid-($C_2$–$C_5$) polyol esters. Particularly useful in the practice of the present invention are the fatty alcohols, such as lauryl, cetyl, oleyl and stearyl alcohols or mixtures thereof, and the fatty acid-polyol esters, i.e., glyceryl monostearate, which is commercially available as Cerasynt® Q from van Dyk & Co., Belleville, N.J. In one class of emulsions useful in the practice of the present invention, all or a part of the emollient oil, isostearyl neopentanoate, or Ceraphyll® 375, is replaced with one of the emollient waxes of the Softisan® Series (Dynamit Nobel Chemicals, Rockleigh, N.J.), a fragrant emollient ester of the class of compounds designated as triglycerides of $C_{10}$–$C_{18}$ saturated fatty acids, which allows the use of less fragrance, thus resulting in a cost savings. An especially useful member of this series is Softisan® 100. Preferably, emollient waxes will make up about 3–10% of the composition, most preferably about 3.5–8%.

VII. Polyhydric Alcohol Emollient

The emulsions of the present invention will also include one or more polyhydric alcohol emollients which are preferably $C_2$–$C_5$ alkanols substituted with 2–4 hydroxyl groups, such as propylene glycol, glycerol, and sorbitol. Polyhydric alcohol emollients will preferably make up 5–15% by weight of the emulsion. One especially preferred mixture of polyhydric alcohol emollients is an about 1:1 mixture of propylene glycol and glycerol.

Therefore, preferred emulsions useful in the present invention may be formulated so as to contain about 50–85% water, about 4–12% emollient oil, about 3.0–10% emollient wax stabilizer, about 5–20% polyhydric alcohol emollient, and about 0.5%–10% organic, water-soluble surfactant, and optionally, about 0.025–0.75% antibacterial preservative and about 0.1 to 0.5% fragrance.

The following ingredients were combined in the weight percentages indicated in Table IV to form a moisturizing composition by the procedure described below.

TABLE IV

| INGREDIENT | PERCENT | GRAMS |
| --- | --- | --- |
| Group A | | |
| Glyceryl Monostearate | 5.0 | 750.0 |
| Cetyl Alcohol | 0.5 | 75.0 |
| Mineral Oil | 5.0 | 750.0 |
| i-Stearyl Neopentanoate | 3.0 | 450.0 |
| Propyl Parabens | 0.10 | 15.0 |
| Butyl Parabens | 0.05 | 7.5 |
| Group B | | |
| Water (deionized) | 62.15 | 9,322.5 |
| Methyl Parabens | 0.30 | 45.0 |
| Propylene Glycol | 5.00 | 750.0 |
| Glycerol | 5.00 | 750.0 |
| Lauryl Dimethyl Amine Oxide (29–31% Solution in $H_2O$) | 3.0 | 450.0 |
| Group C | | |
| Water | 5.0 | 750.0 |
| Sodium Lauryl Sulfate | 0.50 | 75.0 |
| Fragrance | 0.30 | 45.0 |
| Water | 5.0 | 750.0 |
| Kathon CG (Preservative) | 0.10 | 15.0 |
| Total | 100.00 | 15,000.0 |

The oil-phase ingredients of Group A were mixed and heated to 75° C. The water-phase Group B ingredients were separately mixed, heated to 75° C. and then the Group A ingredients were added with good agitation. Stirring was contained for 10 minutes and a 23° C. solution of the Group C ingredients was added subsurface to the stirred 72° C. mixture. The emulsion was stirred and cooled to 45° C. at which point the fragrance was added. The mixture was stirred until its temperature fell to 35° C. The mixture was allowed to stand overnight and then the preservative solution was added with stirring. The mixture was stirred for 45 minutes and then used to impregnate a sheet of Crown Textile C-785 (1.25 oz/yd$^2$) via a Meyer Rod to form a one-use cosmetic applicator pad (0.25 g per 1.5 square inches of fabric).

The resultant applicator sheets were moist but not sticky or unduly wet to the touch and readily applied a clear, non-sticky, homogenous film of the emollient emulsion to dry skin surfaces. The film retained these desirable characteristics when the skin was moistened prior to use of the applicator. As noted above, an effective anti-acne amount of retinoic acid can optionally be combined with this emollient composition.

VIII. Steroids

To treat skin irritations and other dermatological conditions such as various dermatoses, including chronic neurodermatitis, nummular dermatitis, atopic dermatitis, and psoriasis; eczema, poison plant rashes, insect bites and rashes due to cosmetics, detergents, jewelry and the like, on or more of the reservoir populations of the present invention may be impregnated with an effective dermatological amount of one or more steroids, such as a corticosteroid. The sheet may be impregnated with a dry powder of the steroid or steroids, optionally in combination with a solid inert carrier such as starch, talcum powder, dextrin, microcrystalline cellulose and the like. Preferably, the steroid is impregnated into the sheet in combination with a pharmaceutically acceptable carrier, i.e., in combination with a suitable liquid lotion or emulsion, or an ointment or gel.

The percentage of the steroid present in the vehicle can be varied widely, depending on the potency of the steroid with respect to the condition to be treated, but can range from about 0.025–0.05% in the case of corticosteroids such as betamethasone dipropionate or fluocinide, up to as much as 1–5% in the case of hydrocortisone or cortisol.

Useful corticosteroids, their dermatological indications and dosages are disclosed in *Remington's Pharmacuetical Sciences,* A. Osol, ed. Mack Publishing, Easton, Pa. (16th ed. 1980) at pages 898–912, which is incorporated by reference herein, and include betamethasone, cortisol, dexamethasone, flumethasone, fluocinolone, fluorometholone, flurandrenolide, methylprednisolone, prednisolone, desoximetasone, diflorasone, triamcinolone, and their nontoxic organic acid salts such as the benzoate, acetate, valerate, pivalate, acetonide, acetonoide-acetate, diacetate, butyrate, dipropionate salts and the like.

In combination with the appropriate carrier the steroid will be impregnated into the applicator sheet so that, upon application of the sheet to the afflicted skin area, an effective amount of steroid will be delivered to the skin, e.g., from about 500 μg to 250 mg of total steroid per m$^2$ of skin, depending upon the steroid or steroids present in the composition.

Two representative steroid-containing compositions comprising mixtures of organic solvents as the carrier vehicle are given in Table V below.

TABLE V

| | Steroid Solutions | |
|---|---|---|
| | Formulation (wt-%) | |
| Ingredient | A | B |
| Propylene glycol | 86.18 | 82.95 |
| Isopropyl alcohol | 12.00 | 7.00 |
| m-Pyrrol | 1.75 | — |
| Carbitol | — | 10.00 |
| Betamethasone dipropionate | 0.64 | — |
| Fluocinonide | — | 0.05 |

The steroid can also be microencapsulated or stabilized by absorption onto or into dextrin or cyclodextrin particles by methods known to the art.

As noted above, when a steroid-containing composition is included in one of the reservoir populations, the other reservoir population can contain dermatological agents which complement or enhance the activity of the steroid. Such ingredients include antihistamines, antibiotics, e.g., in combination with the carrier vehicles described above, emollient compositions such as those disclosed above, antifungal agents, sunscreens as disclosed above, and compositions which will enhance penetration of the steroid into the skin. The latter compositions include those which, following their application, form an occlusive barrier or film over the applied film of steroid containing composition. Such barrier-forming compositions include those which comprise solvent dissolved or dispersed film-forming polymers such as polysaccharides, polyvinylalcohols, polyacrylate salts, and/ or cross-linked polyacrylate hydrogels.

Any of the above-described compositions can be preformulated and applied to the sheets by spraying, spotting, or brushing techniques well known to the art.

Each composition will be absorbed into a single sheet in an amount effective to provide a unit dosage of each of the bioactive ingredients therein. It is to be understood that such a dose can vary widely, as it will be based on the size of the skin area to be treated, and the nature and severity of the dermatological condition to be treated. For example, the amount of a given semi-liquid or gelled composition delivered to the skin of the user may vary from as little as 0.25–0.5 g to as much as 1–3 g, depending upon the choice of the active ingredient, the size of the sheet and the material of which it is constructed and the skin area and condition to be treated. Thus, the amount of active ingredient delivered as a unit does can be preselected, using the weight percentages provided hereinabove as guidelines.

In practice, the user, e.g., a human afflicted with ache, would wet his/her face or other skin surface, expose the medicated sheet and apply it manually to the afflicted skin area. A mixture of antibiotic- and peroxide-containing vehicles or the dermatological agent combination would be released onto the skin of the user, preferably in a homogenous, even film.

All patents, patent applications and other documents cited herein are incorporated by reference. The invention has been described with reference to various specific and preferred embodiments and techniques. However, it should be understood that many variations and modifications may be made while remaining within the spirit and scope of the invention, and the invention is not to be construed as limited to the specific embodiments shown in the drawings.

What is claimed is:

1. A medicated sheet for applying a plurality of dermatological agents to the skin, the medicated sheet comprising a base sheet consisting of a one-piece flexible absorbent sheet, the medicated sheet further comprising a first area on said base sheet impregnated with a first solid or semi-solid composition comprising a first dermatological agent and a second area on said base sheet impregnated with a second solid or semi-solid composition comprising a second dermatological agent, wherein said first area and said second area are separate and distinct from each other on said base sheet and wherein said first and second compositions are water soluble or water dispersible so that said first and second compositions are released from the base sheet when the sheet is contacted with water, so as to simultaneously and coextensively apply said first and second dermatological agents onto the skin.

2. The medicated sheet of claim 1 wherein said first area further comprises a plurality of first reservoirs, each of said first reservoirs being impregnated with said first composition, and said second area further comprises a plurality of second reservoirs, each of said second reservoirs being impregnated with said second composition.

3. The medicated sheet of claim 1 wherein said first and second areas are substantially equal in size.

4. The sheet of claim 1, 2 or 3 wherein the first dermatological agent is an effective anti-acne amount of a peroxide.

5. The sheet of claim 4 wherein the first dermatological agent comprises benzoyl peroxide.

6. The sheet of claim 4 wherein the first area is impregnated with a first gelled anhydrous composition comprising an effective anti-acne amount of an organic peroxide, about 40–50% of a mixture of organic emollient oils, about 10–13% fatty alcohol, and about 20–30% of an organic gelling agent.

7. The sheet of claim 6 wherein the composition further comprises about 1–10% of a nonionic surfactant.

8. The sheet of claim 4 wherein the second dermatological composition comprises an effective anti-acne amount of an antibiotic selected from the group consisting of erythromycin, tetracycline, clindamycin, meclocycline and the pharmaceutically acceptable salts thereof; about 10–25% of a fatty alcohol, about 20–30% of an organic gelling agent and about 45–55% of a mixture of emollient organic oils.

9. The sheet of claim 8 wherein the second composition further comprises an effective amount of an anionic surfactant to adjust the pH to physiologically acceptable levels.

10. The sheet of claims 1, 2 or 3 wherein the first dermatological agent is an effective keratolytic amount of salicylic acid, azelaic acid or a mixture thereof.

11. The sheet of claim 8 wherein the first dermatological agent is an effective keratolytic amount of salicylic acid, azelaic acid or a mixture thereof.

12. The sheet of claim 10 wherein the first composition comprises an aqueous-alcohol gel comprising about 0.5–10% salicylic acid.

13. The sheet of claim 12 wherein the gel comprises about 0.5–5% of an organic gelling agent.

14. The sheet of claims 1, 2 or 3 wherein the first dermatological agent is an effective anti-acne amount of retinoic acid.

15. The sheet of claim 14 wherein the first dermatological composition comprises about 0.01–0.25% retinoic acid.

16. The sheet of claim 15 wherein the first dermatological composition further comprises a gelled mixture of water with a water-miscible organic solvent.

17. The sheet of claim 14 wherein the first dermatological composition comprises about 0.01–25% retinoic acid, about 50–85% water, about 4–12% emollient oil, about 3–10% emollient wax stabilizer, about 5–20% polyhydric alcohol emollient and about 0.5–10% organic, water-soluble surfactant.

18. The sheet of claim 14 wherein the second dermatological composition comprises an effective amount of one or more sunscreen compounds.

19. The sheet of claim 18 wherein the second dermatological composition comprises about 50–85% water, about 4–12% emollient oil, about 3–10% emollient wax stabilizer, about 5–20% polyhydric alcohol emollient and about 0.5–10% organic, water-soluble surfactant.

20. The sheet of claims 1, 2 or 3 wherein the first dermatological agent is an effective dermatological amount of a corticosteroid in combination with a pharmaceutically acceptable carrier.

21. The method of claim 20 wherein the corticosteroid is dispersed throughout the sheet as a powder.

22. The method of claim 20 wherein the second dermatological agent is an antihistamine, an antibiotic, an antifungal agent, a sunscreen, an emollient or a film-forming polymer.

23. A medicated sheet for applying a dermatological agent to the skin, the medicated sheet comprising a base sheet consisting of a flexible absorbent sheet, the medicated sheet further comprising an array of preselected areas on said base sheet, each of said preselected areas being separated from each other, wherein said areas are impregnated with a solid or semi-solid composition comprising an effective anti-acne amount of a peroxide.

24. The medicated sheet of claim 23 wherein the peroxide is benzoyl peroxide.

25. The medicated sheet of claim 23 wherein the areas are impregnated with a gelled anhydrous composition comprising an effective anti-acne amount of an organic peroxide.

26. The medicated sheet of claim 25 wherein the composition comprises about 1–20% of an organic peroxide, about 40–50% of a mixture of organic emollient oils, about 10–30% fatty alcohol and about 20–30% of an organic gelling agent.

27. The medicated sheet of claim 25 wherein the composition further comprises about 1–10% of a nonionic surfactant.

28. The medicated sheet of claim 25 wherein the peroxide is absorbed on an inert particulate carrier.

29. A method of administering a dermatological agent to a human comprising applying the medicated sheet of claim 1 to wet skin so as to deliver an effective amount of a peroxide to the skin.

* * * * *